United States Patent [19]
Miwa et al.

[11] Patent Number: 5,942,224
[45] Date of Patent: *Aug. 24, 1999

[54] THERAPEUTIC AGENT FOR CAT RESPIRATORY DISEASES AND METHOD OF TREATMENT USING THE SAME

[75] Inventors: Yoshikatsu Miwa; Takatoshi Tamura; Hitoshi Murasaki, all of Tokyo; Masakazu Mitsuhashi, Okayama, all of Japan

[73] Assignee: Kabushiki Kaisha Hayashibara Seibutsu Kagaku Kenkyujo, Okayama, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/578,060

[22] Filed: Dec. 22, 1995

Related U.S. Application Data

[63] Continuation of application No. 08/224,748, Apr. 7, 1994, abandoned.

[30] Foreign Application Priority Data

Apr. 9, 1993 [JP] Japan ................................. 5-105914

[51] Int. Cl.$^6$ .................................................. A61K 38/21
[52] U.S. Cl. ........................ 424/85.7; 424/85.4; 530/351
[58] Field of Search .......................... 530/351; 424/85.4, 424/85.7

[56] References Cited

U.S. PATENT DOCUMENTS

| | | | |
|---|---|---|---|
| 4,276,282 | 6/1981 | Sugimoro et al. | 424/85 |
| 4,462,985 | 7/1984 | Cummins, Jr. | 424/85 |
| 4,820,514 | 4/1989 | Cummins | 424/85.4 |
| 4,820,515 | 4/1989 | Cummins | 424/85.7 |
| 4,855,134 | 8/1989 | Yamahira et al. | 424/85.7 |
| 5,019,382 | 5/1991 | Cummins, Jr. | 424/85.4 |
| 5,194,381 | 3/1993 | Yanni et al. | 435/172.3 |

FOREIGN PATENT DOCUMENTS

| | | |
|---|---|---|
| 5415881 | 12/1981 | Japan . |
| 8803411 | 5/1988 | WIPO . |

OTHER PUBLICATIONS

Mitsunaya, J. Tokyo Med. Coll., vol. 44(2) pp. 191–200, 1986, Abstract.
Cummins et al., J. Biol. Resp. Mod., vol. 7(5), pp. 513–523, 1988.
Krakowka et al., Vet. Immunol. Immunopath., vol. 19, pp. 185–196, 1988.
Imanishi, J. et al., J. Interferon Res., vol. 1(1), pp. 169–178, 1980.
Seahorn, Thomas et al., Am. J. Vet. Res., vol. 51(12), pp. 2006–2010, 1990.
Roney C. S et al., Am. J. Vet. Res., vol. 46(6), pp. 1251–1255, 1985.
Bryson D. G et al., Vet. Rec., vol. 125(25), pp. 615–618, Dec. 1989.
Scherbakova et al., Antiobiotiki, vol. 18(3), pp. 256–259; 1973 CA 78:143766.
Cocker et al, Effect of human α–hybrid interferon on the course of feline viral rhinotracheitis , The Veterinary Record, vol. 120, pp. 391–393, 1987.
Fulton et al, Susceptibility of Feline Herpesvirus 1 and a Feline Calicivirus to Feline Interferon and Recombinant Human Leukocyte Interferons, Antimicrobial Agents And Chemotherapy, vol. 28, No. 5, pp. 698–699, Nov. 1985.
Sen et al, Antiviral and Protein–Inducing Activities of Recombinant Human Leukocyte Interferons and Their hybrids, Journal Of Virology, vol. 50, No. 2, pp. 445–450, May 1984.
Young et al, The History of Interferon and its use in Animal Therapy, East African Medical Journal, vol. 67, No. 7, pp. ss.31–22.63, Jul. 1990.
Cantell, K. et al. "Large–scale Production of Human Leukocyte Interferon Containing $10^8$ Units per ml." J. Gen Virol. (1978), vol. 39, pp. 541–543.
Uchino, Tomiya et al. Shodobutsu–Rinsho. vol. 11, No. 6, pp. 11–25 (1992).

*Primary Examiner*—Chhaya D. Sayala
*Attorney, Agent, or Firm*—Browdy and Neimark

[57] ABSTRACT

A method using a therapeutic agent for cat respiratory diseases which contains a human interferon as an effective ingredient. The therapeutic agent exerts a strong efficacy on cats with only a small dose even if administered to them orally or parenterally, and reduces the labor and burden of veterinaries and cat owners by a large margin.

15 Claims, No Drawings

THERAPEUTIC AGENT FOR CAT RESPIRATORY DISEASES AND METHOD OF TREATMENT USING THE SAME

This application is a continuation of application Ser. No. 08/224,748, filed Apr. 7, 1994 abandoned.

BACKGROUND OF THE INVENTION

1. Field of the Invention

The present invention relates to a medicament for animals directed to cats, more particularly to a therapeutic agent for cat respiratory diseases which contains a human interferon(s) (sometimes abbreviated as "HuIFN(s)" hereinafter) as an effective ingredient.

2. Description of the Prior Art

Recently, the number of people, who find their daily lives enriched by their pet animals has been increasing as their incomes and life-styles improve. Among pet animals, especially cats and dogs have been the most popular from antiquity, and a variety of species of these animals have been produced by successive breedings for many years. Some of these species are amazingly costly. As is evident from the above-mentioned recent tendency, the number of tame cats has been remarkably increasing, and this results in an increase of cats being brought to veterinary hospitals.

Excluding cats with traumas and fractures requiring surgery, the number of other cats suffering from infectious diseases, especially respiratory diseases, i.e. "feline cold", and being brought to veterinary hospitals, is increasing. The main inducer of feline cold has been deemed to be viruses which infect feline airways, and felines infected with viruses mostly show common cold-like symptoms such as cough, rhinorrhea, drooling, fever, inflammation of superior airway, pneumonia, stomatitis, glossitis, conjunctivitis, granular adenitis, lingual ulcer, ulcer of nasal end, systematic skin ulcer, turbinal ulcer, scours, vomiting, anorexia and reduction of vitality. More particularly, when felines are infected with feline immunodeficiency virus (sometimes abbreviated as "FIV" hereinafter), they become more likely to show the above-mentioned symptoms and rapidly weaken. At present, there exists no treatment worth mentioning for feline virus diseases as well as feline respiratory diseases, and actually these diseases are only treated with symptomatic treatments such as trophotherapy by administering to felines to be treated nutrient feeds in order to relieve their dehydration symptoms and to recover their physical vitality, as well as administering antibiotics to them to prevent multiple or secondary infections, and physically removing viscous secreta.

Recently, it was reported by Tomiya UCHINO et al., in *Shodobutsu-Rinsho*, Vol.11, No.6, pp.11–25 (1992) that an intravenous administration of several millions of international units of a recombinant feline interferon to a feline suffering from respiratory diseases exerted a considerably-high therapeutic effect. In order to attain the desired effect, the administration, however, requires a very large amount of feline interferon, and this subjects their owners to an excessive economical burden: The increment of the owners's economical burden is unavoidable because biologically active polypeptides such as interferons, even though they are recombinant types, are generally too expensive, and because successive administrations of such interferons further increases their economical burden. In general, cats requires very careful handling because of their nervousness and great wariness, so that other administrations, excluding intravenous administration, which attain a satisfactory efficacy, are favorably employed by veterinarians who actually treat cats.

Thus, the development of methods to more loosely treat cat respiratory diseases with satisfactorily-high efficacy, as well as to reduce the financial burden their owners has been in great demand.

SUMMARY OF THE INVENTION

In view of the foregoing, the object of the present invention is to provide a therapeutic agent for cat respiratory diseases which exerts a satisfactorily-high efficacy even when administered to cats via administrations excluding intravenous administration, and to reduce the burdens and labor to veterinaries who treat cats, as well as reduce the cost of treatment to the owners.

The present inventors have eagerly pursued studies to attain the above-mentioned object and found that HuIFNs exert a strong efficacy on the improvement of cats with clinical symptoms in general such as cough, rhinorrhea, drooling, fever, inflammation of superior airway, pneumonia, stomatitis, glossitis, conjunctivitis, granular adenitis, lingual ulcer, ulcer of nasal end, systematic skin ulcer, turbinal ulcer, scours, vomiting, anorexia and reduction of vitality. The administrations of HuIFNs are not restricted to intravenous administration, and can be arbitrarily administered to cats by other administrations such as oral- and parenteral-administrations.

Thus, the present inventors accomplished a therapeutic agent for cat respiratory diseases which contains an HuIFN as an effective ingredient.

DETAILED DESCRIPTION OF THE INVENTION

In has been said that interferons (IFNs), which had been originally found as a substance with a virus-inhibitory activity, have a strict species specificity, and because of this no efficacy would be expected without administering to animals with homogeneous interferons. Therefore, the fact that human interferons per se are effective on the treatment of cat respiratory diseases has never been reported.

The HuIFNs used as an effective ingredient in the present therapeutic agent effectively act on cats suffering from respiratory diseases and improve their clinical symptoms in general which were accompanied by the diseases, for example, cough, rhinorrhea, drooling, fever, inflammation of superior airway, pneumonia, stomatitis, glossitis, conjunctivitis, granular adenitis, lingual ulcer, ulcer of nasal end, systematic skin ulcer, turbinal ulcer, scours, vomiting, anorexia and reduction of vitality.

The HuIFNs used in the invention exert a relatively-high efficacy on cat respiratory diseases, and, usually the desired efficacy is attained with only a small dose of about 0.005–5,000 international units of the HuIFNs per kg of cat.

The HuIFNs exert a strong therapeutic efficacy on cat respiratory diseases even when administered to them orally and parenterally, as well as intravenously.

The present invention is explained more in detail by the following Examples, etc:

The wording "cat(s)" as referred to in the invention means felid(s) or feline(s) of the genus Felis in general who is susceptible to airway-infectious viruses such as feline herpes virus and calicivirus, and shows one or more clinical symptoms in general selected from cough, rhinorrhea, drooling, fever, inflammation of superior airway, pneumonia, stomatitis, glossitis, conjunctivitis, granular adenitis, lingual ulcer, ulcer of nasal end, systematic skin ulcer, turbinal ulcer, scours, vomiting, anorexia and reduction of vitality when it is infected with the above-mentioned viruses or further infected multiply or successively with FIV, mycoplasma, bacteria or parasites. The therapeutic agent according to the present invention is usually directed to tame cats in general.

The present therapeutic agent according to the present invention contains as an effective ingredient an interferon derived from human cells or recombinant microorganisms and animal cells into which an HuIFN related gene, prepared from human cells, has been introduced. At the present time, HuIFNs are mainly classified into 3 types, namely HuIFN-α, HuIFN-β and HuIFN-γ based on their antigenicity. These HuIFNs can be used in the present invention, though they show a slight difference in their therapeutic efficacy on cat respiratory diseases. The HuIFNs can be used alone or in combination with two or more different types of interferons. It is preferable to use the HuIFNs with the highest possible specific activity, and partially or completely purified specimens with a specific activity of about $10^5$ international units/mg protein or higher can be favorably used for oral use, while purified HuIFN specimens with a specific activity of about $10^7$ international units/mg protein or higher can be favorably used for parenteral use.

Experiments conducted by the present inventors revealed that among these HuIFNs an HuIFN-α, particularly, "a natural HuIFN-α", produced by leukocytes isolated from human blood or by human lymphoblastoid cell lines such as BALL-1 cells and Namalwa cells, is characteristic in that it exerts a relatively-high therapeutic efficacy on cat respiratory diseases with only a relatively-low level of side effects. More particularly, the HuIFN-α derived from BALL-1 cells, containing interferon subtypes α2 and α8 in a satisfactorily balanced ratio, exerted the maximum therapeutic efficacy when used in the present invention. Generally, recombinant HuIFNs seemed to be inferior to natural HuIFNs in the therapeutic efficacy, and showed a tendency to cause a slightly-higher level of side effects.

The present therapeutic agent for cat respiratory diseases includes those consisting of HuIFNs alone or in combination with other physiologically acceptable substances such as a carrier, excipient, diluent, adjuvant and stabilizer, and, if necessary antipyretic, anti-inflammatory agent, antibacterial agent, digestion accelerating agent, nutrient agent and feed. The present therapeutic agent includes those in the form of a unit dose which contain an HuIFN in an amount requisite for one day dose or in an amount of 1/40 to 4 times of the daily dose. The therapeutic agents in the form of a unit dose mean those in the form of a physically separated agent, for example, those in the form of an injection, liquid, orally administrable gel agent, powder, granular, tablet, capsule and sublingual.

Now explaining the dose and use of the present therapeutic agent, it exerts the desired therapeutic efficacy whenever administered to cats orally and parenterally. Although the dose varies dependently on the species of cats, the variety of causative virus, symptoms of cats, amounts of the HuIFNs used in the invention, administration routes, and interferon types to be used, the HuIFNs are usually administered to cats 1–3 times a day or 1–5 times a week at a dose of about 0.005–5,000 international units, preferably about 0.5–50 international units, more preferably about 1–20 international units per shot over a period of about one day to one month.

When the present therapeutic agent is administered to cats orally, it is first prepared into an orally administrable form such as a liquid, troche, powder, granule, tablet, sublingual and feed, then administered to the cats in usual manner into their oral-, nasal-, esophagus- and gastric-cavities by using adequate supplementary administration aids such as a sound and instrument for oral administration. In the case of parenterally administering to cats the present therapeutic agent in the form of injection, it can be administered to them intracutaneously, subcutaneously, intravenously and intraperitonealy. The experiments of the present therapeutic agent conducted by the present inventors revealed that the desired therapeutic effect could not be attained when the dose was below the above administration range, while when the dose exceeded the range the levels of both unfavorable side effects and formation of antibodies increased, and the owners's economical burden became unbalanced in comparison with the therapeutic effect. Based on these results, we decided the aforementioned administration range is the most favorable.

When compared the administration routes in terms of their therapeutic efficacy and readiness of administrations, oral administration has an advantage of being readily conducted at each owner's home in general, but has the disadvantage of being not readily conducted to administer a prescribed amount of HuIFN to cats. This may result in an excessive amount of an HuIFN administration as compared with the desired doses, as well as in a relatively-long period of time for therapy and a heavy economical burden to cat owners. On the contrary, parenteral administration has the disadvantage of being not readily conducted at each owner's home in general, but has an advantage of being conducted to administer an accurate amount of HuIFN to the cats, and being attainable of the desired therapeutic efficacy with only the minimum dose of HuIFN. Therefore, the parenteral administration attains the complete treatment of cats within the shortest possible period of time, and lowers the owners's economical burden. More particularly, the intracutaneous-, subcutaneous- and intramuscular-administrations of the present therapeutic agent are readily conducted and attain the desired therapeutic efficacy with only a small amount of HuIFN than in the case of the oral administration and other administrations excluding the aforesaid administrations, as well as satisfactorily reducing the owners's economical burden. These advantageous features were more distinct in the case of natural HuIFNs, more particularly HuIFN-α derived from BALL-1 cells.

Throughout the specification, the HuIFN activity is expressed with "international interferon units": Assaying an HuIFN specimen on the microtiter technique for determining the degree of the cytopathic-inhibitory activity of Sindbis virus on FL cells, and calculating the activity based on an activity obtained with "Ga23-901-532", an international HuIFN standard of National Institutes of Health, U.S.A.

The following Examples explain the present invention more in detail:

EXAMPLE 1

Dehydrated Injection

In accordance with the method in Japanese Patent Publication No.54,158/81, BALL-1 cells proliferated in hamsters were subjected to the action of sendai virus (HVJ) in a nutrient culture medium to induce an interferon. The resultant culture was centrifuged to obtain a supernatant which was then concentrated and partially purified on affinity chromatography using phenyl sepharose to obtain a partially purified HuIFN with a specific activity of about $10^6$ international units/mg protein. The partially purified HuIFN was in usual manner further purified on affinity chromatography using "NK-2 SEPHAROSE", a product of Celltech Ltd., Berks, England, wherein an anti-HuIFN-α monoclonal antibody was immobilized on water-insoluble carriers, and subjected to gel filtration chromatography using a gel column equilibrated with phosphate buffer (pH 7.0) containing about 0.1 mg/ml of cat serum albumin. Thus, a solution containing a purified HuIFN-α with a specific activity of about $2 \times 10^8$ international units/mg protein was obtained.

The solution thus obtained was concentrated with a membrane filter into a solution containing about 5 mg protein/ml HuIFN-α which was then diluted with a physiological saline containing one w/v % cat serum albumin and 0.01 M phosphate buffer (pH 7.0) to obtain a solution with a concentration of 15 international units/ml of the HuIFN-α, followed by membrane filtration and sterilization thereof. One ml aliquots of the resultant solution were aseptically injected into vials and lyophilized.

Since the product contains an HuIFN-α derived from BALL-1 cells as an effective ingredient and a serum albumin from cat as an excipient, it can be favorably used as a therapeutic agent for cat respiratory diseases.

EXAMPLE 2

Dehydrated Injection

Leukocytes separated from human blood by conventional method were subjected to the action of sendai virus (HVJ) to induce HuIFN which was then purified in accordance with the method as described by Kari Cantell et al. in *The Journal of General Virology*, Vol.39, pp.541–543 (1978) to obtain a partially purified HuIFN with a specific activity of about $2 \times 10^6$ international units/mg protein. Similarly as in Example 1, the partially purified HuIFN was successively purified on affinity chromatography using an anti-HuIFN-α monoclonal antibody, and gel filtration chromatography using a gel column equilibrated with a phosphate buffer (pH 7.0) containing about 0.1 mg/ml of a purified gelatin as listed in the Pharmacopoeia of Japan to obtain an HuIFN-α solution containing a purified HuIFN-α with a specific activity of about $2 \times 10^8$ international units/mg protein.

The solution thus obtained was concentrated with a membrane filter into a solution containing about 5 mg protein/ml of the HuIFN-α, which was then diluted with a physiological saline containing 0.01 M phosphate buffer (pH 7.0) and 1 w/v % purified gelatin as listed in Pharmacopoeia of Japan into a solution with a concentration of 20 international units/ml of the HuIFN-α, followed by membrane filtration and sterilization thereof. One ml aliquots of the resultant solution were aseptically injected into vials and lyophilized.

Although the product, containing the HuIFN-α derived from human leukocytes as an effective ingredient, is slightly inferior to the product in Example 1 in terms of therapeutic effect and side effects, it can be favorably used as a therapeutic agent for cat respiratory diseases.

EXAMPLE 3

Dehydrated Injection

Similarly as in Example 1, a purified HuIFN-α specimen, prepared by allowing sendai virus (HVJ) to act on BALL-1 cells, was diluted in physiological saline containing 3 w/v % cat serum albumin and 0.1 M phosphate buffer (pH 7.0) to give a concentration of 20,000 international units of the HuIFN-α. The resultant solution was membrane filtered, sterilized and injected into vials by one ml.

Similarly as the product in Example 1, the product, containing a purified HuIFN-α derived from BALL-1 cells as an effective ingredient and a serum albumin derived from cat as an excipient, can be suitably used as a therapeutic agent for cat respiratory diseases.

EXAMPLE 4

Oral Gel Agent

One w/v % calf serum albumin was dissolved in distilled water, and the resultant solution was mixed with a solution containing a partially purified HuIFN derived from BALL-1 cells prepared by the method in Example 1 into an HuIFN solution containing 300 international units of the HuIFN per g. Thirty-three parts by weight of the solution was mixed with a solution prepared by dissolving 0.5 parts by weight of "Tween 80", a surfactant, in 15.0 parts by weight of ethanol, and the resultant mixture was mixed with a solution prepared by dissolving 0.5 parts by weight of triethanolamine in 15.0 parts by weight of glycerine. To the resultant mixture was added a small amount of triethanolamine to obtain a roughly neutral gel preparation containing about 100 international units of the HuIFN per ml.

The product, which contains an HuIFN derived from BALL-1 cells as an effective ingredient and has an appropriate residence time in cat mouths, is a readily-swallowable oral gel agent for cat respiratory diseases.

EXAMPLE 5

Powdered Agent

One hundred parts by weight of "FINETOSE®", a high-purity anhydrous crystalline maltose commercialized by Hayashibara Co., Ltd., Okayama, Japan, was homogeneously sprayed with 2 parts by weight of a solution containing about $10^6$ international units/ml of a partially purified HuIFN derived from human leukocytes prepared by the method in Example 2, and the resultant mixture was dried in vacuo, pulverized and sieved to obtain granules having a grain size of 100–500 μm. The granules were mixed to homogeneity with an adequate amount of "FINETOSE®" to obtain a powdered agent containing about 100 international units of the HuIFN per g, d.s.b.

The product, which has a satisfactory storage stability and an appropriate residence time in cat mouths, is suitably used as a therapeutic agent for cat respiratory diseases. The product is a readily-swallowable powdered agent which has a moderate sweetness and less stimulates cat mouths when administered to their oral cavities.

EXAMPLE 6

Granule

Fifteen parts by weight of an aqueous solution containing about 30,000 international units/ml HuIFN, prepared with a partially purified HuIFN derived from BALL-1 cells obtained by the method in Example 1, was mixed to homogeneity with 100 parts by weight of "FINETOSE®", a high-purity anhydrous crystalline maltose commercialized by Hayashibara Co. Ltd., Okayama, Japan, and the resultant mixture was subjected to a granulator to obtain granules.

The product containing about 4,400 international units of the HuIFN per g, d.s.b., and has a satisfactory storage stability, and is suitably used as a therapeutic agent for cat respiratory diseases. The product is a readily-swallowable granule for cats because it has a moderate sweetness and less stimulates the oral cavities when orally administered.

The followings are the clinical tests of the present therapeutic agents in the aforementioned Examples:

EXPERIMENT REFERENCE 1

Clinical Test

Fifty-two tame cats were actually administered with the present therapeutic agent and observed their symptoms, and the therapeutic efficacy and side effects were evaluated, wherein said cats, which had been mainly suffering from cough, rhinorrhea, drooling, fever, inflammation of superior airway, pneumonia, stomatitis, glossitis, conjunctivitis, granular adenitis, lingual ulcer, ulcer of nasal end, systematic skin ulcer, turbinal ulcer, scours, vomiting, anorexia and reduction of vitality, were brought to a veterinary hospital and diagnosed as cat respiratory diseases.

Thirty-three male cats and 19 female cats, estimated ages of 1–6-year-old, which had been diagnosed as cat respiratory diseases based on their diagnoses in general observed in their first medical examinations and diagnosed as FIV-antibody positive carriers from virus diagnosis, were injected every day with the dehydrated injection of Example 1 to their subcutaneous of cervixes at a dose of about 1–20 international units/shot/day/kg cat of HuIFN-$\alpha$ over a period of one week. Immediately after the initiation of administrations, the cats were carefully observed, and the administration doses and the following 14 clinical symptoms in general such as systematic conditions, dehydrating conditions, appetites, requiring for water, activities, rhinorrhea, cough, scours, drooling, conjunctivitis, stomatitis, ulcer of nasal end, respirating conditions, and vomiting were recorded. The virus diagnosis of the cats revealed that most of the cats were suspicious of a multiple infection of FIV and cat herpes virus and/or cat calicivirus.

The veterinarians mainly conducted the clinical test and controlled the dose and administration frequency of interferon while observing the conditions and symptoms of cats as well as side effects. After completion of the administrations, the results were put together and the therapeutic efficacy of the dehydrated injection was evaluated based on the following criteria: Cats who recovered their health within 5 days were evaluated as "Superior"; those, wherein the symptoms of stomatitis were improved as compared with those in their first medical examinations, and 3 or more other symptoms were improved or 5 of the other symptoms were improved without causing stomatitis, were evaluated as "Effective"; those, wherein the symptoms of stomatitis were not improved but 4 or more other symptoms were improved, were evaluated as "Slightly effective"; those, who showed no improvement in their symptoms, were evaluated as "Non effective"; and those, wherein the symptoms were worsened, were evaluated as "Inferior".

The results in the clinical test revealed that all the cats recovered their health from cough, rhinorrhea, drooling an scours within 3 days or immediately after the initiation of administration, and their temperatures recovered to a normal level of 37° C. Every cat remarkably improved or even recovered the health from inflammation of superior airway, stomatitis, conjunctivitis, and ulcer of nasal end within a week after the initiation of the administration, as well as improving appetite and activity. Judgement based on the above-mentioned criteria revealed that 52 clinical cases were grouped into 28 cases of "Superior", 15 cases of "Effective", 5 cases of "Slightly effective", 4 cases of "Non effective", and non of "Inferior". Among 52 cases the total percentage of the cases of "Superior", "Effective" and "Slightly effective" reached to about 92%. During the administration period, no significant side effects was observed, and this evidenced that the present therapeutic agent is satisfactorily effective for cat respiratory diseases without a fear of causing side effects. An antibody formation, which might be induced by the administered HuIFN-$\alpha$, was not observed in some cats, who had been continuously diagnosed their blood after recovery of their health. This indicates that the present therapeutic agent can be administered repeatedly to the same cat to treat his or her respiratory disease without a fear of causing side effects.

Based on the above findings, the therapeutic agents in Examples 2, 4 and 5 were similarly subjected to their clinical tests which resulted in an exertion of a relatively-high therapeutic efficacy, i.e. their therapeutic efficacy were about 70% or higher when parenterally administered and about 60% or higher when orally administered. The efficacy of the oral administrations was slightly lower than that of the parenteral administrations but it was far higher than those of medicaments in general. Since the parenteral administrations were conducted by intradermal-, intraperitoneal-, intramuscular-, intravenous- and intraperitoneal-injection with only a small amount of dose, the time required for such an injection was relatively short, and almost every injection completed with only one shot without letting nearly all the cats go wild.

The purified and partially purified HuIFN and HuIFN-$\alpha$ specimens used in Examples 1, 2, 4 and 5 were tested with healthy cats for their acute toxicity to reveal that their toxicity were considerably low.

EXPERIMENT REFERENCE 2

Clinical Test

Forty tame cats, which had the same symptoms as those used in Experiment reference 1 and were diagnosed as cat respiratory diseases, were administered with the dehydrated injection of Example 3, and observed, followed by the evaluation of the efficacy and side effects.

Nineteen male cats and 21 female cats, estimated ages of 1–6-year-old, which had been diagnosed as cat respiratory diseases based on their diagnoses in general observed in their first medical examinations and diagnosed as FIV-antibody positive carriers from virus diagnosis, were injected every day with the dehydrated injection of Example 3 to the subcutaneous of their backs at a dose of about 500–5,000 international units/shot/day/kg cat of HuIFN-$\alpha$ over a period of one week. Immediately after the initiation of administrations, the cats were carefully observed, and the administered doses and the 14 clinical symptoms as indicated in Experiment reference 1 were recorded.

The veterinarians mainly conducted the clinical test and controlled the dose and the administration frequency of interferon while observing side effects as well as conditions and symptoms of the cats. After completion of the administrations, the results were put together and the therapeutic efficacy of the dehydrated injection was evaluated based on the same criteria as indicated in Experiment reference 1.

The results in the clinical test revealed that all the cats were improved their symptoms immediately after the initiation of administration, and they recovered from cough, rhinorrhea, drooling and scours within 3 days, and recovered their normal temperatures in the level of 37° C. They were also remarkably improved their health or even cured from inflammation of superior airway, stomatitis, conjunctivitis, and ulcer of nasal end within a week after the initiation of administration, as well as being improved their appetite and activity.

Judgement based on the above-mentioned criteria revealed that 40 clinical cases were grouped into 25 cases of "Superior", 11 cases of "Effective", 2 cases of "Slightly effective", 2 cases of "Non effective", and non of "Inferior". Among these 40 cases the total percentage of the cases of "Superior", "Effective" and "Slightly effective" reached to 95%. During the administration period, no significant side effects were observed, and this evidenced that the present therapeutic agent is satisfactorily effective for cat respiratory diseases without a fear of causing side effects. No antibody formation, which might be induced by the administered HuIFN-α, was observed in some cats, who had been continuously diagnosed their blood after recovery of their health. This indicates that the present therapeutic agent can be used without a fear of causing side effects even when administered repeatedly with a dose of about 500–5,000 international units of the HuIFN-α per kg of the weight.

Based on the above findings, the therapeutic agent in Example 6 was similarly subjected to its clinical test, and this resulted in a relatively-high therapeutic efficacy, i.e. the therapeutic efficacy was about 75% or higher even when administered orally. The efficacy attained by the oral administration was slightly lower than that attained by the parenteral administrations but the efficacy was far higher than that attained by conventional medicaments.

The purified and partially purified HuIFN and HuIFN-α specimens used in Examples 3 and 6 were tested with healthy cats for their acute toxicity to reveal that their toxicity were considerably low.

ACUTE TOXICITY TEST

Cat serum albumin and a partially purified HuIFN or a purified HuIFN-α derived from BALL-1 cells prepared by the method in Example 1 or 2, or derived from human leukocytes prepared by the method in Example 1 or 2, were dissolved in this order in a physiological saline containing 0.01 M phosphate buffer (pH 7.0) to give the final concentrations of 0.1 w/v % and $1 \times 10^6$ international units/ml respectively. Four different solutions were respectively administered subcutaneously or orally to 4 groups of cats, each group consisting of 5 healthy mongrel cats, estimated ages of 1–2-year-old, at a dose of $1 \times 10^6$ international units/kg cat of the HuIFN or HuIFN-α, corresponding to 200 times of the maximum dose of the present therapeutic agent, and observed. As a control, the same volume of physiological saline, similarly prepared as above except for not dissolving any HuIFN specimen therein, was administered to cats by the same administration route.

As a result, no statistically significant difference was observed both in test- and control-groups. No cat died after the HuIFN administrations, and no significant change was observed in terms of their health conditions in general, weights and appetites after and before the HuIFN administrations. These results indicate that the toxicity of the present therapeutic agent is satisfactorily low when administered to cats.

As described above, the present therapeutic agent for cat respiratory diseases which contains an HuIFN as an effective ingredient satisfactorily improves the cat clinical symptoms in general such as cough, rhinorrhea, drooling, fever, inflammation of superior airway, pneumonia, stomatitis, glossitis, conjunctivitis, granular adenitis, lingual ulcer, ulcer of nasal end, systematic skin ulcer, turbinal ulcer, scours, vomiting, anorexia and reduction of vitality.

The present therapeutic agent reduces the owners's economical burden by a large margin because it contains as an effective ingredient HuIFNs which can be administered to cats without a fear of causing side effects even if administered to them with a relatively-large amount, and exert a strong efficacy on the aforementioned clinical symptoms with only a small amount. For the same reason, the present therapeutic agent renders the intravenous administration of human interferons unnecessary, and attains the desired efficacy even when administered to cats via the oral and parenteral routes such as intradermal-, subcutaneous- and intramuscular-administrations. Thus, the present therapeutic agent does facilitate the administration of a prescribed amount of HuIFNs to nervous and careful cats without fail, and reduces the labor and burden of veterinaries as well as their assistants by a large margin.

These advantageous effects are more augmented when a natural HuIFN-α, more particularly, an HuIFN-α derived from BALL-1 cells is used as the effective ingredient of the present therapeutic agent.

Thus, the present invention, which exerts the aforementioned satisfactory effects, is a great invention contributive to the filed.

While there has been described what is at present considered to be the preferred embodiments of the present invention, it will be understood the various modifications may be made therein, and it is intended to cover in the appended claims all such modifications as fall within the true spirits and scope of the invention.

We claim:

1. A therapeutic agent for cat respiratory diseases induced by viral infection of feline airways, which is in the form of a dehydrated injection gel, powder or granule, and comprises (i) as an effective ingredient a natural human interferon-α which is derived from BALL-1 cells, and which has a specific activity of at least about $10^5$ international units/mg protein, and (ii) a member selected from the group consisting of cat serum albumin, gelatin, and maltose, said natural human interferon-α being incorporated in said agent in an amount which can be administered to a cat at a dose of about 0.005–5,000 international units per kg of said cat.

2. The therapeutic agent in accordance with claim 1, which is in the form of an oral or parenteral agent.

3. The therapeutic agent in accordance with claim 1 containing a dose of about 0.5–50 international units per kg of said cat.

4. The therapeutic agent in accordance with claim 1 containing a dose of about 1–20 international units per kg of said cat.

5. A method to treat a cat suffering from cat respiratory disease induced by viral infection of feline airways, which comprises a step of administering the therapeutic agent of claim 1 to said cat at a dose of about 0.005–5,000 international units per kg weight of said cat.

6. The method in accordance with claim 5, wherein said natural human interferon-α is orally or parenterally administered to said cat.

7. The method according to claim 5 wherein the dose is about 0.5–50 international units per kg of said cat.

8. The method according to claim 5 wherein the dose is about 1–20 international units per kg of said cat.

9. A veterinary composition for cat respiratory diseases induced by viral infection of feline airways, comprising a natural human interferon-α which is derived from BALL-1 cells, and which has a specific activity of at least $10^5$ international units/mg protein, together with a physiologically acceptable substance selected from the group consisting of cat serum albumin, gelatin, and maltose, said composition being in a unit dosage form containing 0.5–50 international units of said natural human interferon-α.

10. The composition according to claim 9 wherein said unit dosage form contains 1–20 international units of said natural human interferon-α.

11. The veterinary compositions according to claim 9 wherein the dose is about 0.5–50 international units per kg of said cat.

12. The veterinary composition according to claim 9 wherein the dose is about 1–20 international units per kg of said cat.

13. The method according to claim 9 wherein the dose is about 1–20 international units per kg of said cat.

14. A method for treating a cat suffering from a cat respiratory disease induced by viral infection of feline airways, comprising administering to said cat said agent of claim 9 in an amount of about 0.005–5,000 international units per kg weight of said cat of said natural human interferon-α.

15. The method according to claim 14 wherein the dose is about 0.5–50 international units per kg of said cat.

* * * * *